Figure 1:
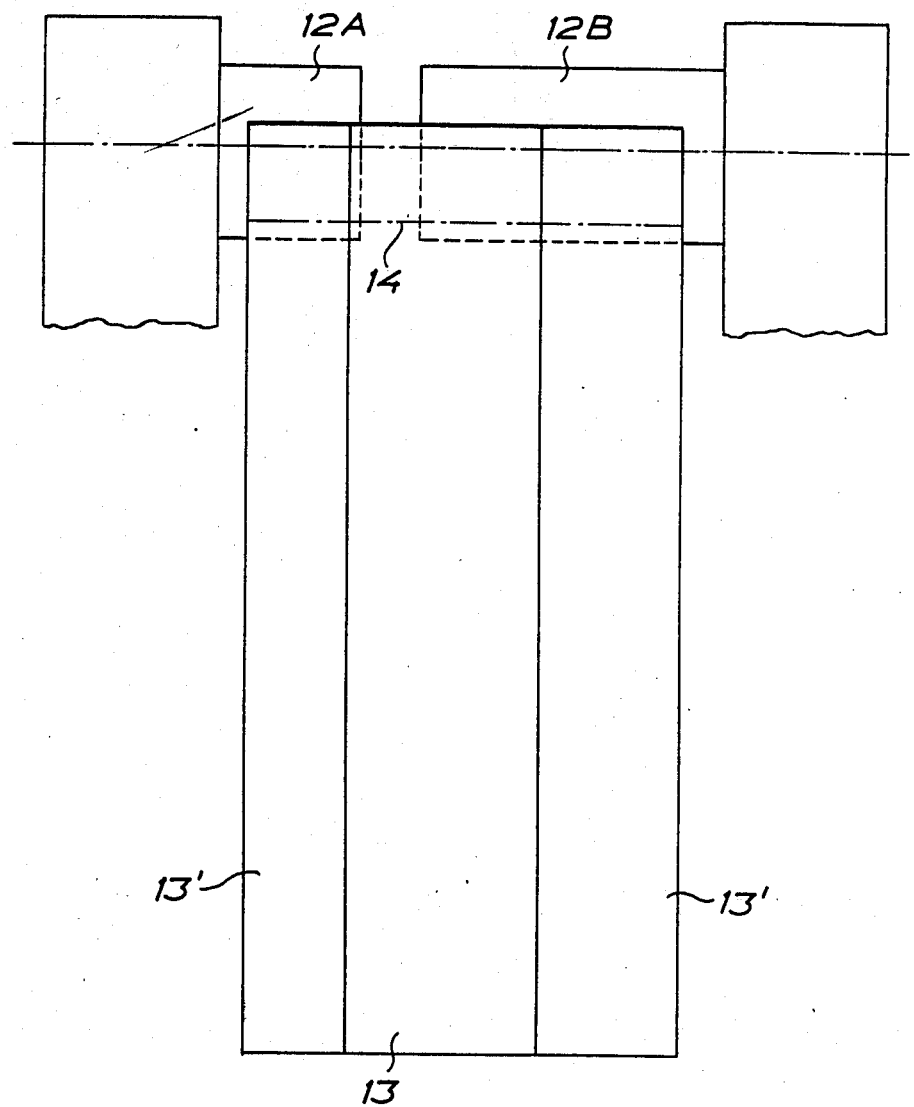

United States Patent [19]

Forsman

[11] Patent Number: 4,675,217
[45] Date of Patent: Jun. 23, 1987

[54] ABSORBING PRODUCT

[76] Inventor: Lars Ö. Forsman, Rörögatan 18, Helsingborg, S-253 72, Sweden

[21] Appl. No.: 568,196
[22] PCT Filed: Apr. 15, 1983
[86] PCT No.: PCT/SE83/00139
  § 371 Date: Dec. 12, 1983
  § 102(e) Date: Dec. 12, 1983
[87] PCT Pub. No.: WO83/03537
  PCT Pub. Date: Oct. 27, 1983

[30] Foreign Application Priority Data

Apr. 15, 1982 [SE] Sweden .................... 8202368

[51] Int. Cl.[4] ............................. B27N 5/02
[52] U.S. Cl. .......................... 428/35; 428/74; 428/121; 428/124; 428/182; 428/222; 428/284; 604/367; 604/385; 604/904
[58] Field of Search ............... 428/35, 283, 74, 121, 428/124, 182, 284, 913, 222; 604/904, 385, 378, 285, 287, 367

[56] References Cited

U.S. PATENT DOCUMENTS 2,328,795 9/1943 Finks ...................... 604/904
4,278,088 7/1981 Reeves et al. ............ 604/904
4,341,214 7/1982 Fries et al. .............. 604/904

Primary Examiner—James J. Bell
Attorney, Agent, or Firm—Merchant, Gould, Smith, Edell, Welter & Schmidt

[57] ABSTRACT

An absorbing product comprising a substantially cylindrical cartridge of a web material (13) with a first inner layer (25) and an intermediate layer (24) which merge into each other at a twisted portion (19) at one end of the cartridge, and a third outer layer (27) which connects to the first layer at another twisted portion (26) at the other end of the cartridge. The inner layer defines a closed cavity between the two twisted portions. The invention also relates to method and apparatus for manufacturing the product. The apparatus has a cylindrical mandrel having two co-axially spaced elements (12A, 12B) which are individually rotatable. In one element there is provided a co-axially displaceable member (20) forming a cavity (21) open towards the other element which is tubular to receive the axially displaceable member with a surrounding gap. A pressure member (23) is axially displaceable through said other mandrel element into the cavity. The method comprises the step of arranging a cartridge (17) of web material on the mandrel, a shorter and a longer portion (17A and 17B, respectively) of the cartridge then being rotated to provide an intermediate twisted portion (19). By pressure against said latter portion the longer cartridge portion (17B) is drawn partly into the shorter cartridge portion (17A), the longer cartridge portion then being twisted between the part that has been drawn and the rest of the cartridge portion which is then turn inside out onto the shorter cartridge portion.

8 Claims, 26 Drawing Figures

ABSORBING PRODUCT

The present invention relates to an absorbing product which can comprise a round wipe-off pad of the type used in medical treatment for wiping-off blood and other body liquids at surgical operations and treatment of injuries and wounds on the human body and also for applying disinfecting agents on skin areas before surgery is performed. However, the absorbing product according to the invention can also be constructed as a tampon, e.g. a menstrual tampon or as means for absorbing liquids in different connections e.g. for absorbing and limiting oil spillage on floors, the ground, or on water.

Round wipe-off pads in available embodiments thereof are made of gauze and are formed as a substantially round ball or a cylindrical pad. In the most common embodiment there is applied inside the pad a rubber string which fixes the gauze and keeps it together in the round shape. The gauze inside such a wipe-off pad is not regularly orientated; it is concentrated to one or more locations, the gauze therein often having been torn in the process of manufacture. If the rubber string breaks, which happens relatively frequently, a rag of gauze with loose threads is left.

As far as conventional menstrual tampons are concerned, there are usually made of carded cotton which is rolled and compacted to a diameter of 12 to 13 mm. Since it is desired that the tampon shall be able to expand radially to about twice the diameter at absorption, it is common to fold the cotton when compacting same. In this manner the circumference is increased at the outer surface such that it will approach the circumference at the double diameter.

The tampon can expand to the maximum volume while absorbing liquid only if it is free. In that condition, the maximum absorption factor is also attained, said factor being defined as $$\frac{\text{absorbed weight} - \text{dry weight}}{\text{dry weight}}$$

When the tampon is inserted into the vagina, it can expand during absorption only until equilibrium is obtained between the expansion force due to the absorption and the contraction force from the walls of the vagina. The expansion force due to the absorption is inversely proportional to the diameter increase, i.e. it decreases in relation to the diameter increase, while the contraction force from the walls of the vagina are substantially proportional to the diameter increase.

The conclusion will be that the tampon practically never can attain the maximum volume attained when the tampon is free. Therefore, also the maximum absorption factor is not obtained. Practical tests with conventional homogenous tampons also have shown that the absorption will be limited when expansion of the tampon is prevented mechanically. The absorbing material proper blocks the absorption.

The Swedish published specification No. 7714725-4 (publication number 422 407) describes a method of manufacturing round wipe-off pads of gauze by which there is obtained a round wipe-off pad which consists of a substantially cylindrical cartridge having an inner layer and an outer layer on the outside thereof, which merge into each other at a twisted portion at one end of the cartridge while the cartridge is folded inwards at the other end. This round wipe-off pad represents a considerable improvement in relation to the round wipe-off pads with a rubber string, because it is held together without a rubber string or other adhering means and does not present any torn irregular material.

The invention relates to a development of the round wipe-off pad according to said published specification, but the object thereof is to provide an absorbing product which is considerably more useful than as a round wipe-off pad only and has a considerably wider range of use. Said round wipe-off pad comprises a substantially cylindrical cartridge of a web material with a first inner layer and a second layer located on the outside of said inner layer, which merge into each other at a twisted portion at one end of the cartridge. The product can be manufactured in a rational manner by an extensively automated process of manufacture which, moreover, is not limited to the traditional gauze but can also be adapted easily to modern highly absorbing materials. The invention also makes possible a further improvement of the absorption ability of the product by using different combinations of material.

The absorbing product according to the invention for this purpose has obtained the characteristics appearing from claim 1, and for the manufacture of this product the invention also provides a method according to claim 5 and an apparatus according to claim 8.

Figure 2:
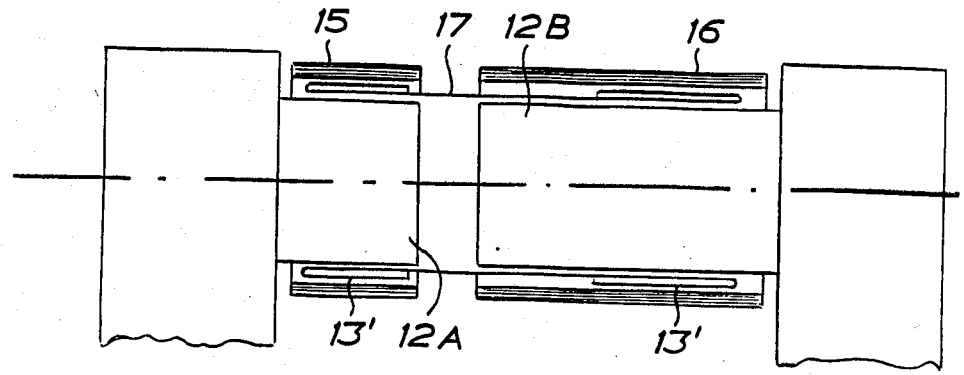
Figure 3:
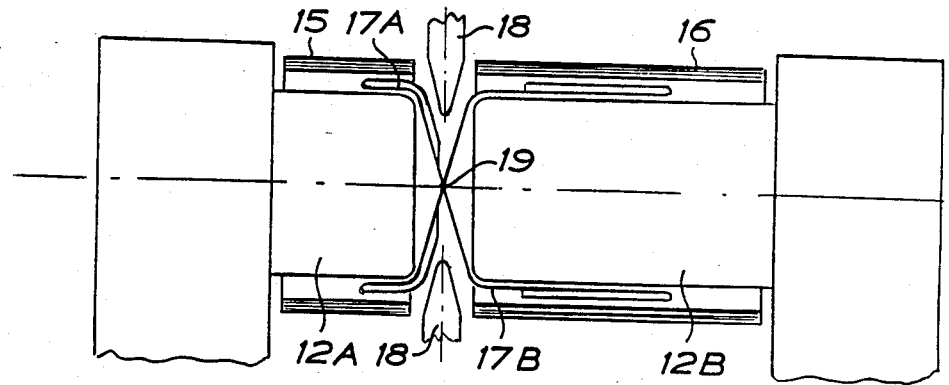
Figure 4:
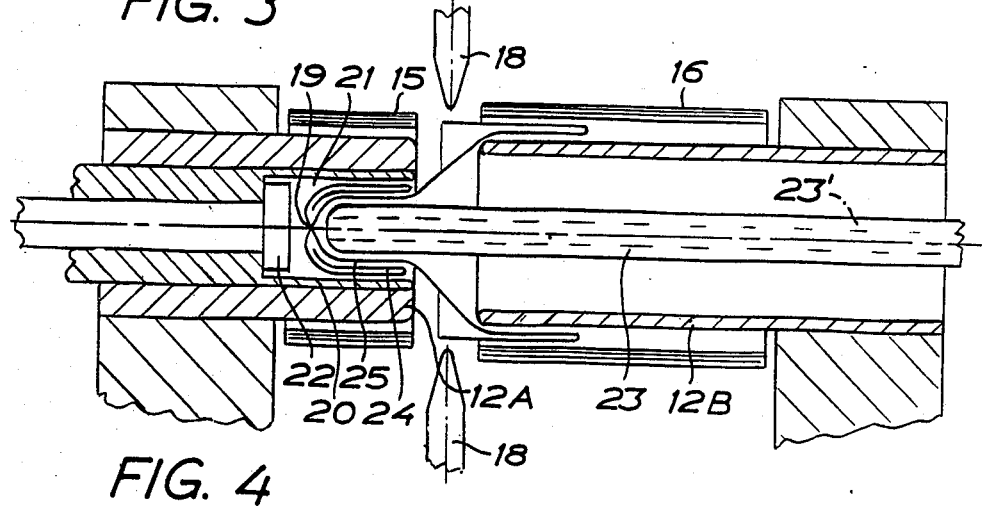
Figure 6:
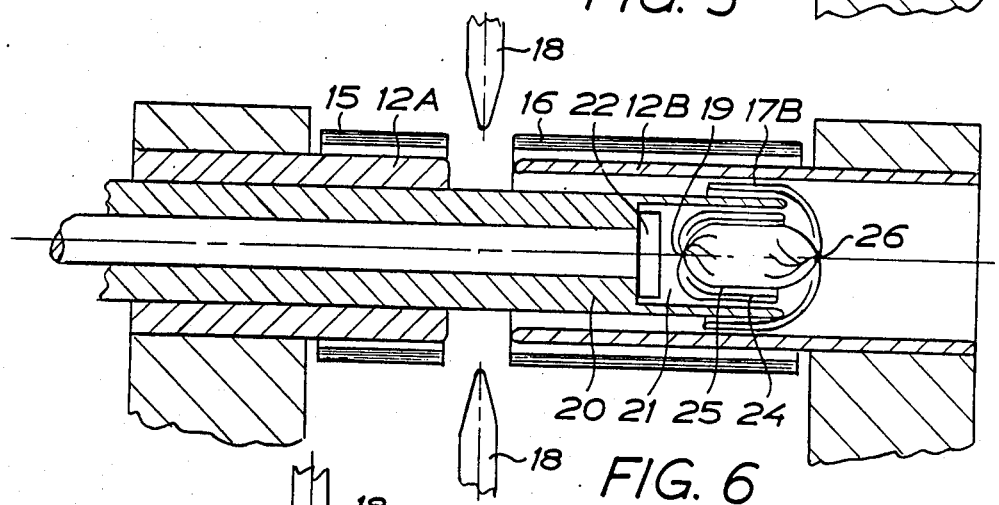
Figure 7:
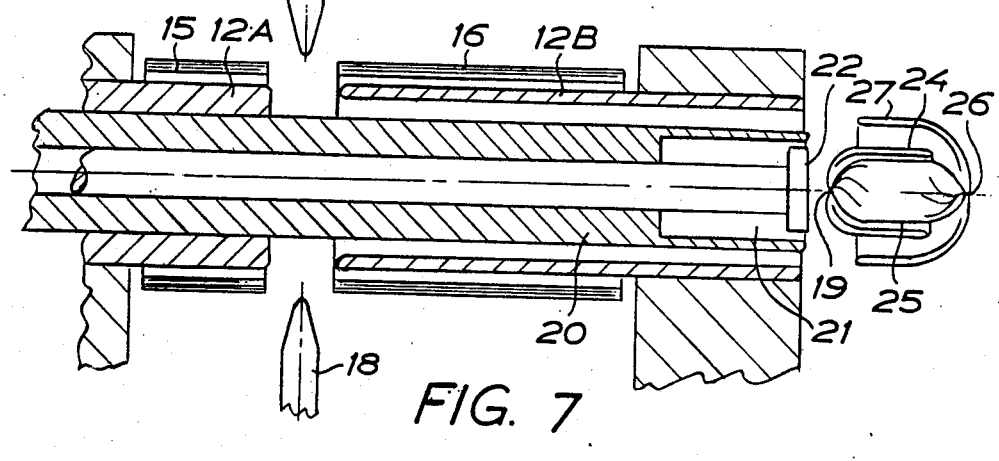
Figure 8:
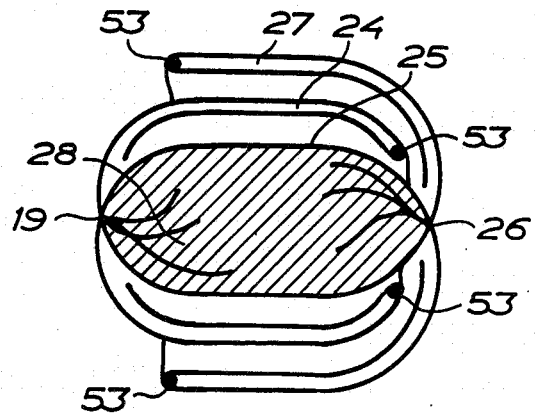
Figure 9:
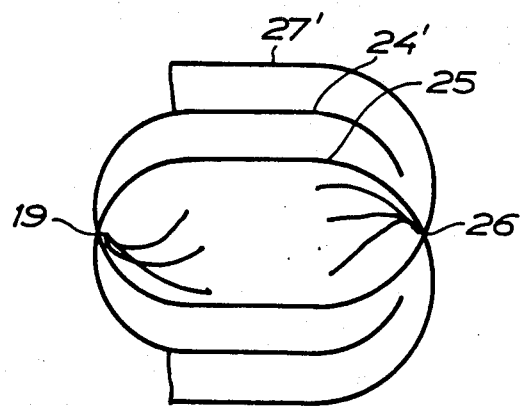
Figure 10:
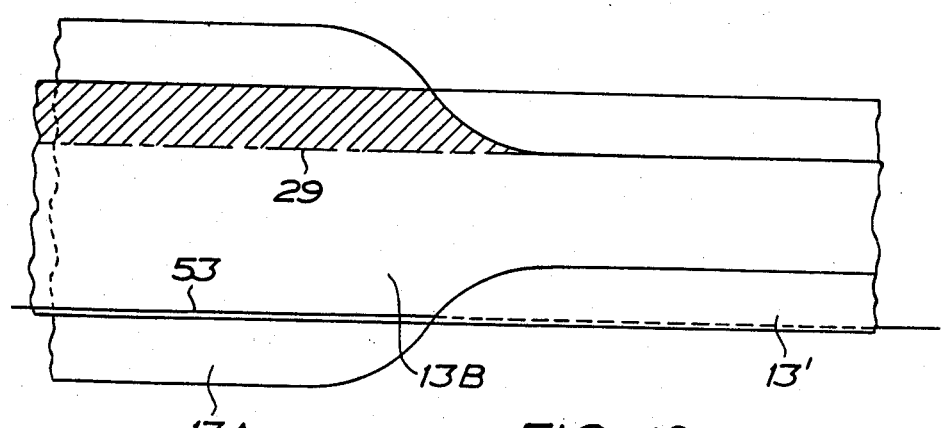
Figure 11A:
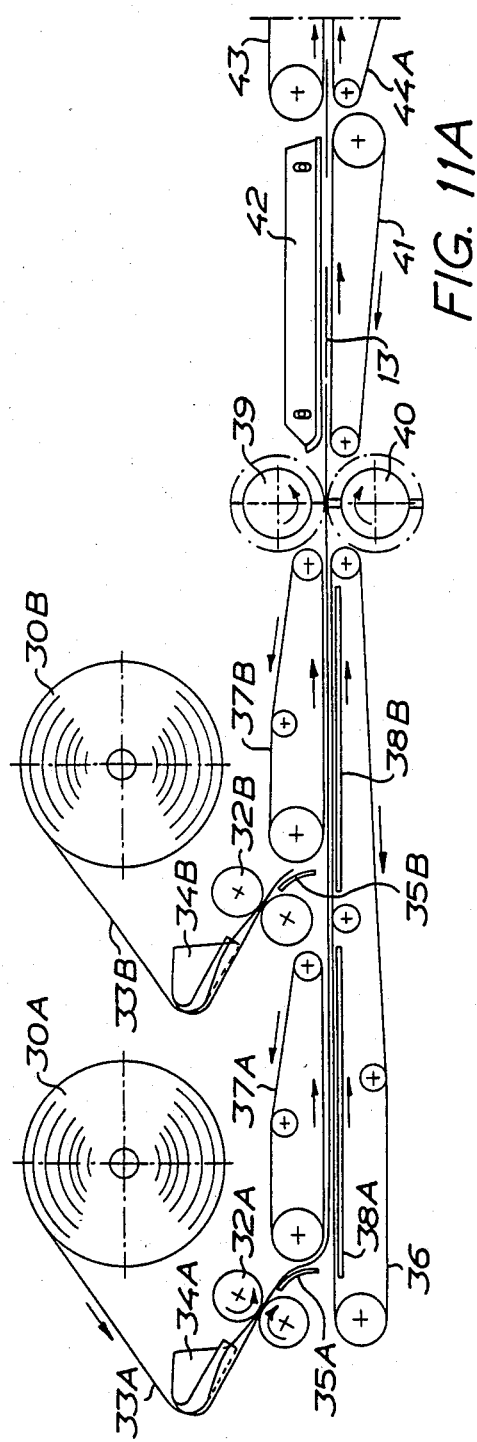
Figure 11B:
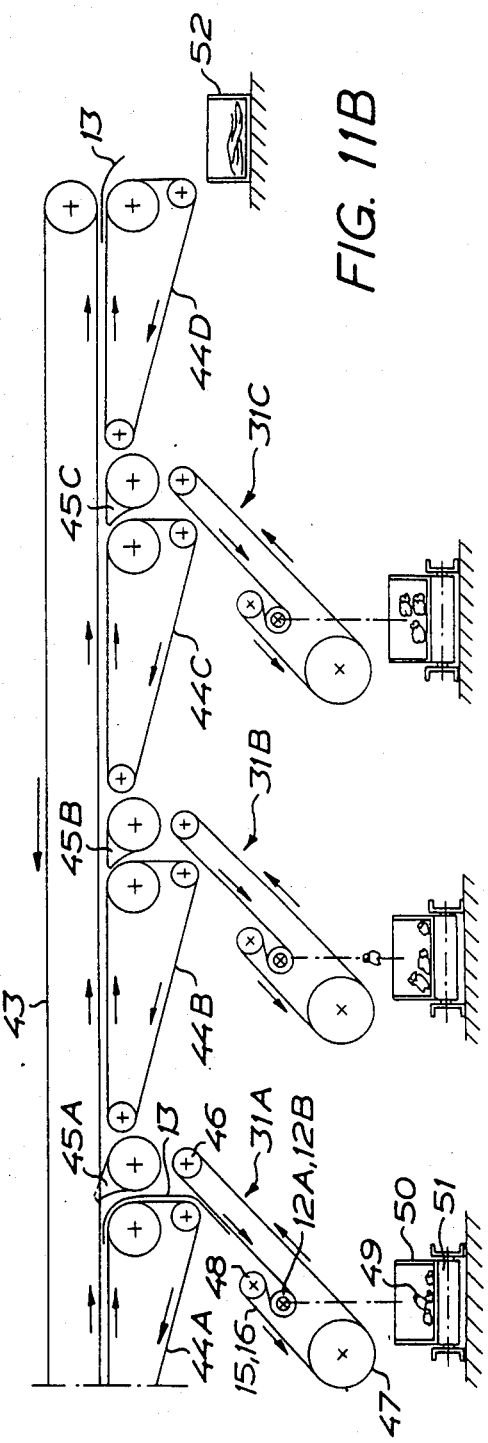
Figure 12:
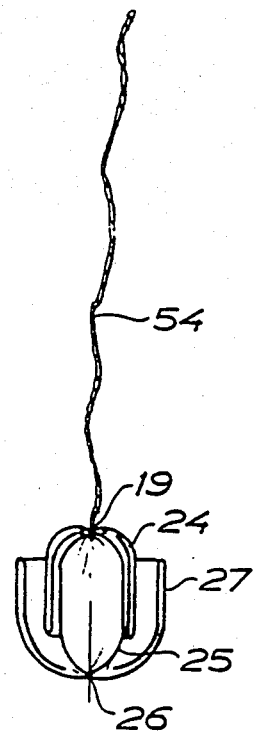
Figure 16:
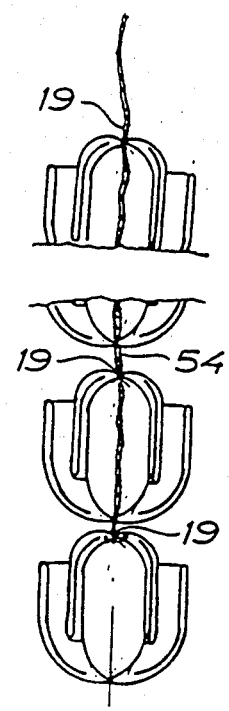
Figure 22:
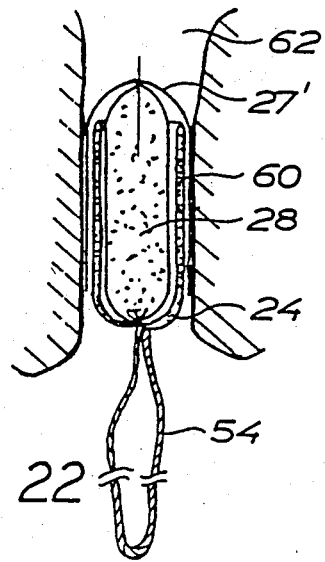
Figure 23:
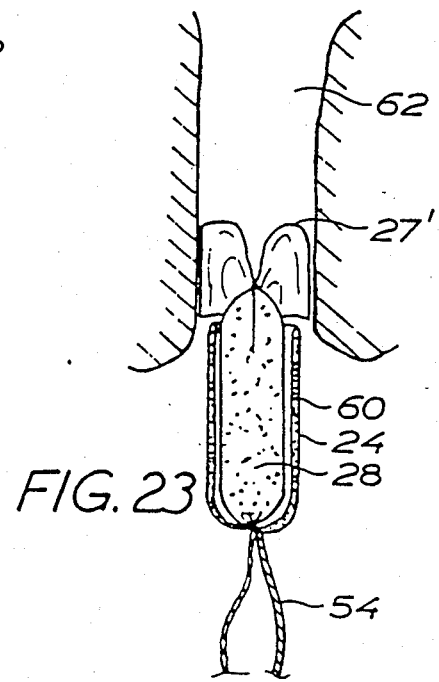
Figure 13:
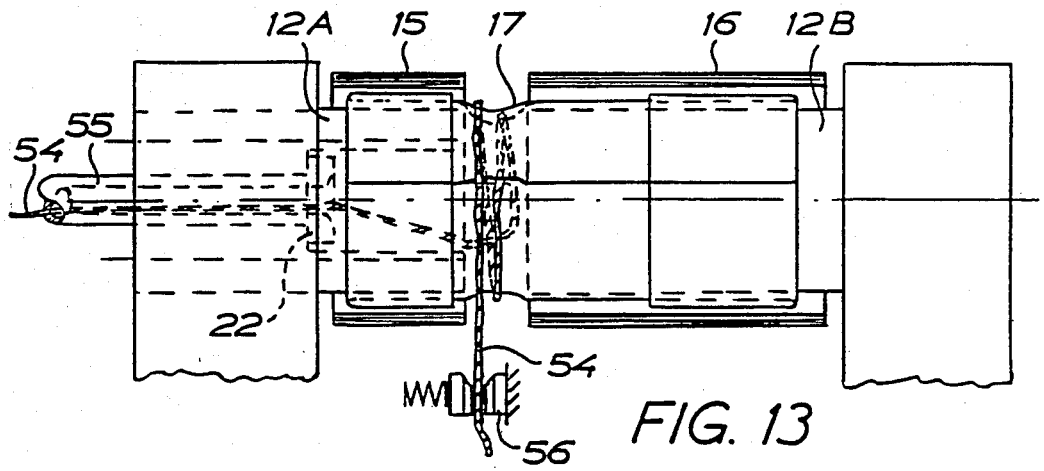
Figure 14:
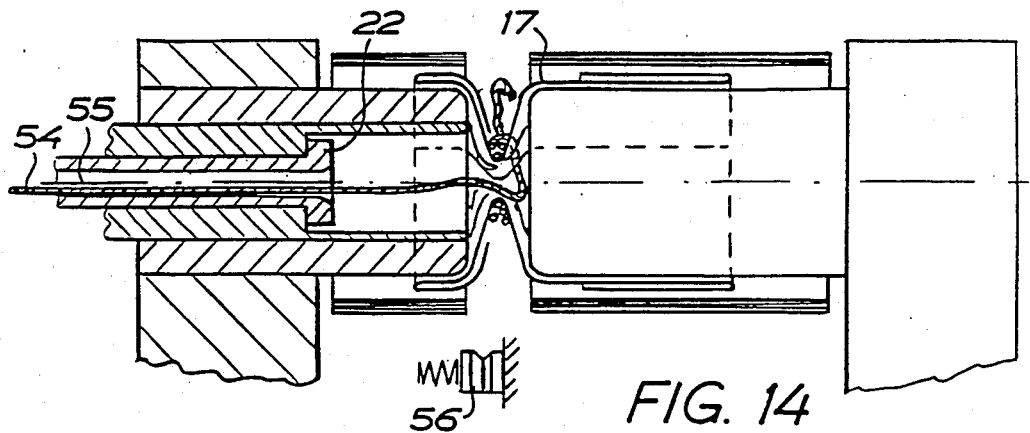
Figure 15:
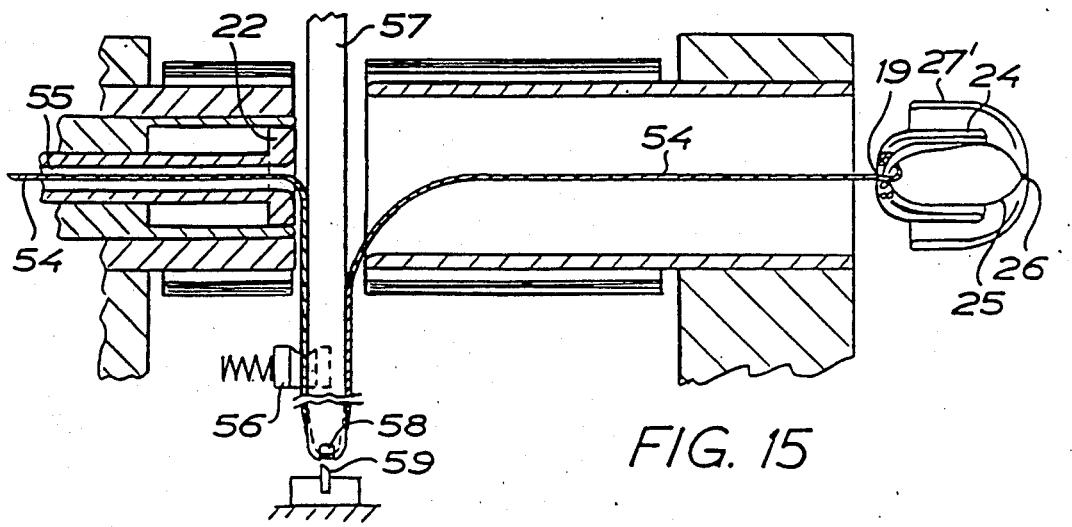
Figure 18:
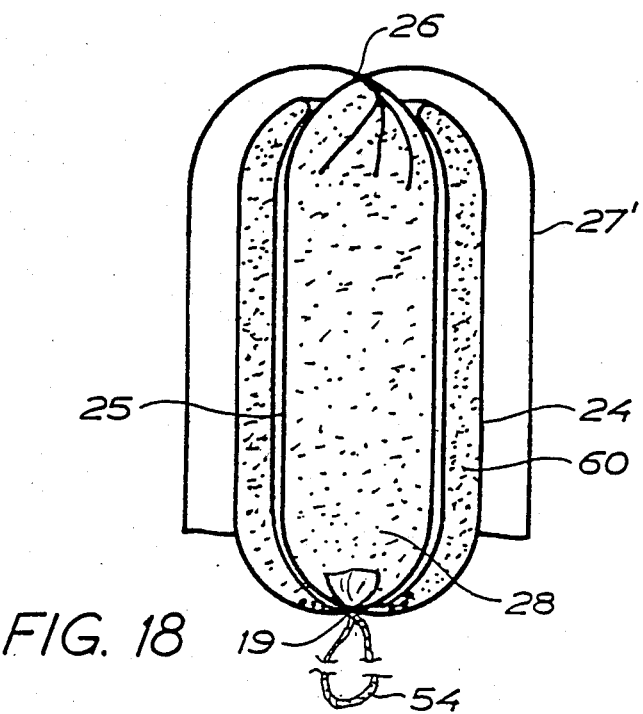
Figure 17:
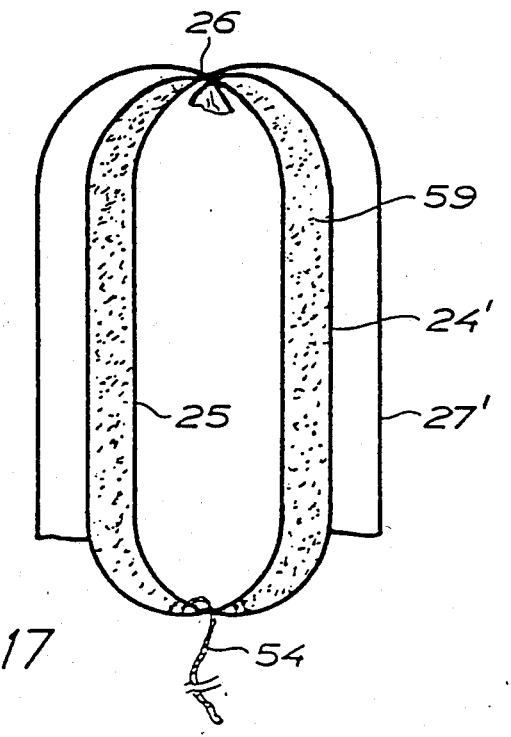
Figure 19:
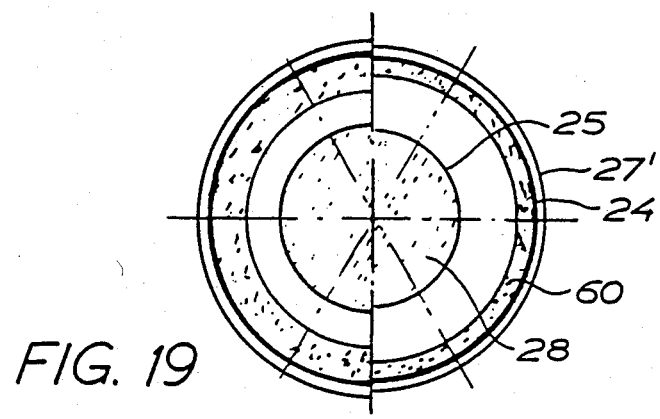
Figure 24:
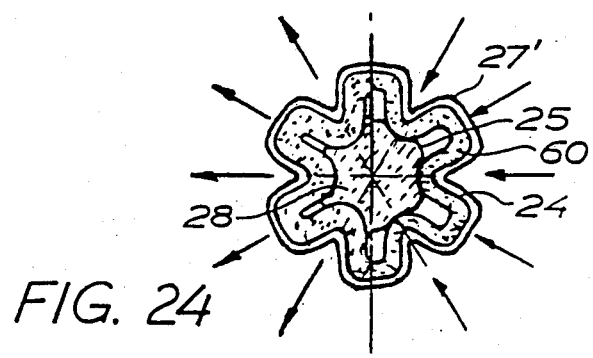
Figure 25:
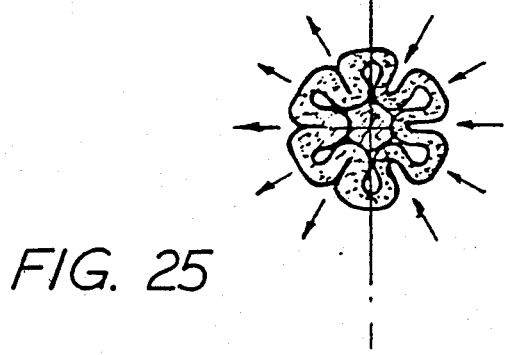
Figure 20:
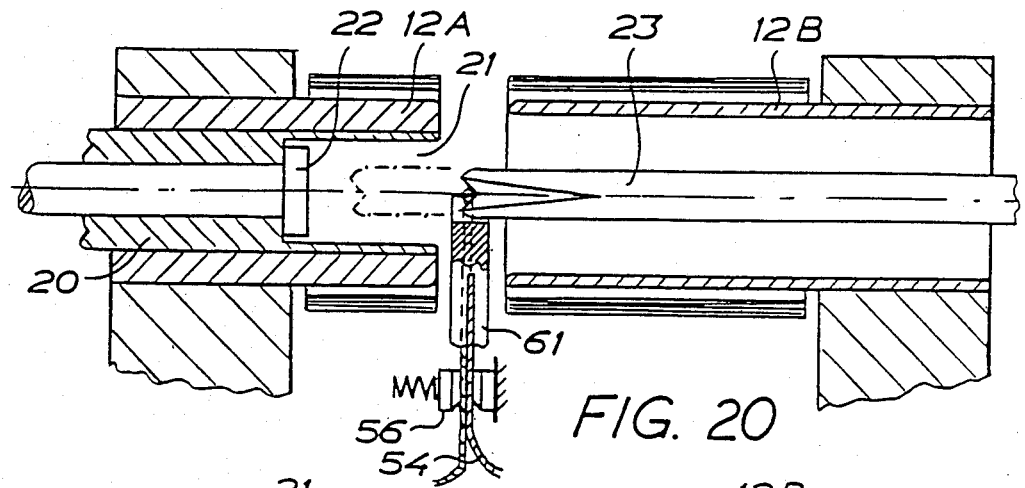
Figure 21:
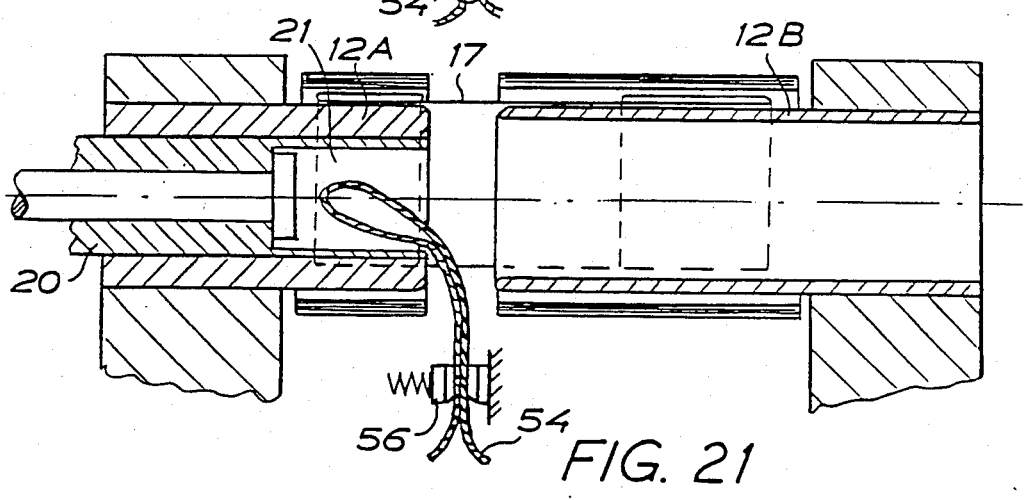

The invention will be explained in more detail below with reference to the accompanying drawings in which FIG. 1 is a diagrammatic plan view which illustrates a first step in the manufacture of the absorbing product of the invention, FIGS. 2 and 3 are corresponding views, partly in axial section, which illustrate two following steps, FIGS. 4 to 7 are axial sectional views which illustrate four further steps in the manufacture of the absorbing product of the invention, FIG. 8 is a diagrammatic axial sectional view of the product manufactured according to the invention, intended as a round wipe-off pad, FIG. 9 is a view corresponding to FIG. 8 of a modified embodiment of the product of the invention, FIG. 10 is a plan view of a web of material for the manufacture of the absorbing product according to the invention by using two different web materials, FIGS. 11A and 11B together are a diagrammatic view of an apparatus for automated manufacture of the absorbing product of the invention, FIG. 12 is a longitudinal sectional view of a round wipe-off pad constructed according to the invention, FIG. 13 is a view similar to FIG. 2 and illustrates a first step of attaching a string to the round wipe-off pad according to FIG. 12, FIGS. 14 and 15 are views similar to FIG. 13 and illustrate two following steps therein attaching the string, FIG. 16 is an axial sectional view of an absorbing "chain product" of the invention, FIG. 17 is an axial sectional view of a tampon of the invention in one embodiment thereof, FIG. 18 is an axial sectional view of a tampon of the invention in a second embodiment thereof, FIG. 19 is a cross-sectional view of the tampon in FIG. 18, FIGS. 20 and 21 are views similar to FIG. 4 and illustrate two different steps in attaching a string formed as an eye, to the tampon according to FIG. 18, FIGS. 22 and 23 are two diagrammatic sectional views illustrating the use of the tampon of FIG. 18 as a menstrual tampon, and FIGS. 24 and 25 are cross-sectional views illustrating a modified embodiment of a menstrual tampon of the invention.

Referring to FIG. 1, there is shown therein a mandrel which comprises two co-axially arranged and individually rotatably mounted elements 12A and 12B, the mandrel element 12A being shorter than the mandrel element 12B. The ends of the mandrel elements facing each other are mutually spaced. The mandrel elements are individually freely rotatable in order that the mandrel elements rotate synchronously in one and the same direction or one element rotates at a higher or lower speed in relation to the other element. A piece of gauze 13 the marginal portions 13' of which are folded-over and which can also have a folded-over end margin as indicated by a dot-and-dash line 14, is engaged with the two mandrel elements 12A and 12B to be wound around the combined mandrel, the engagement being effected by belts 15 and 16, FIG. 2, pressing the web 13 against the combined mandrel. Then, the mandrel elements can be rotated by being carried along by the belts due to the friction between the web and the belts, respectively, and the mandrel elements. The belts 15 and 16 can be driven over conducting rollers in a usual way by separate motors, the rpm of one motor being adjustable in relation to that of the other motor.

By winding the gauze web around the mandrel the web forms a cartridge designated 17 in FIG. 2, and then the step according to FIG. 3 takes place.

Referring to FIG. 3, two jaws or rails 18 are inserted from diametrically opposite sides into the gap between the mandrel elements 12A and 12B to effect a slight depression of the cartridge wall, the speed of one driving belt 15 or 16 at the same time being increased or decreased in relation to the speed of the other driving belt such that the cartridge 17 will be twisted between the ends thereof at the depressions, a shorter cartridge portion 17A being obtained on the shorter mandrel element 12A and a longer cartridge portion 17B being obtained on the longer mandrel element 12B located one at each side of the twisted portion 19. In order to control the lengths of one cartridge portion and the other during this step the belt 15 and 16, respectively, can be individually tensioned more or less at the proper moment such that the resistance against withdrawal of the cartridge from the associated mandrel elements is controlled during the twisting.

As will be seen from FIG. 4 to which reference now is made, the mandrel element 12A as well as the mandrel element 12B is tubular. A plunger 20 is arranged for axial displacement in the mandrel element 12A, said plunger having a cylindrical cavity 21 open towards the mandrel element 12B, an ejector piston 22 being axially displaceable in the cavity 21. In the mandrel element 12B the inside diameter of which is substantially larger than the outside diameter of the plunger 20, a cylindrical rod 23 is axially displaceable, and this rod has a diameter which is substantially smaller than the inside diameter of the cavity 21. When the jaws 18 have been withdrawn, the rod 23 is axially displaced into the cavity 21, while the belts 15 and 16 are running at the same speed or alternatively are stationary, the rod drawing the cartridge portion 17A into the cavity 21 and drawing partly the cartridge portion 17B into the cartridge portion 17A by pressure against the twisted portion 19.

Figure 5:
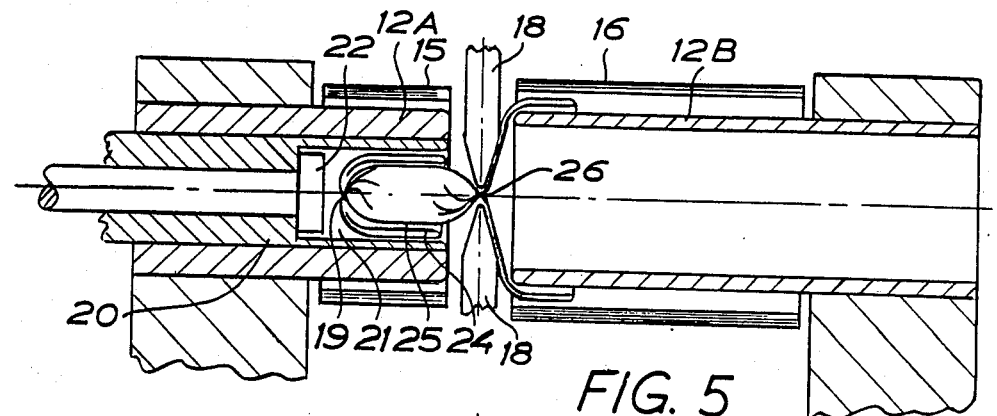

The belts 15 and 16 can form transverse ridges on the surfaces facing the cartridge portions 17A and 17B to carry along more easily the cartridge portions while at the same time allowing axial withdrawal of the cartridge portions from the mandrel elements 12A and 12B. As will be seen from FIG. 4, the cartridge portion now located in the cavity 21 will have an outer double-folded layer, designated 24, which is formed by the cartridge portion 17A, and an inner single layer, designated 25, which is formed by part of the cartridge portion 17B, the layers 24 and 25 merging into each other at the twisted portion 19. Then, the jaws 18 are again displaced towards the cartridge 17, this time towards the cartridge portion 17B between that part thereof which is received by the cartridge portion 17A, and that part thereof which is located outside the cartridge portion 17A and still surrounds the mandrel element 12B as shown in FIG. 5. The jaws are displaced inwards such a distance that the jaws clamp the cartridge portion 17A. With e.g. the belt 15 stationary and the belt 16 running, the cartridge is now twisted again at 26 and then the belt 16 is again stopped and the jaws 18 are withdrawn.

The following step is disclosed in FIG. 6 and in this step the plunger 20 is displaced into the mandrel element 12B, the part of the cartridge portion 17B which was previously located on said mandrel element now being turned inside out over the plunger 20 to form an outer double-folded layer 27 on the cartridge when this is then ejected from the cavity 21 by axial displacement of the piston 22 in the last step according to FIG. 7. The product thus obtained now has the shape diagrammatically shown in FIG. 8 wherein the several layers are somewhat spaced apart to show more clearly the construction of the product; in practice the layers are laying close to each other.

The product can be manufactured in the manner described also of other materials than gauze, e.g. a non-woven material, and in that case it is not necessary to fold-over the margins, because the fibers of such material do not get loose to the same extent as the fibers of gauze. In that case the product will have the appearance shown in FIG. 9, i.e. the layers 24 and 27, designated 24' and 27' in FIG. 9, are not double in this case.

According to a development of the invention, an absorbing particular or fibrous material can be introduced into the cartridge 17 in the step of FIG. 4 through a passage 23' in the rod 23. By the step according to FIG. 5, this material will be enclosed in the cavity defined by the layer 25 and the twisted portions 19 and 26 in the absorbing product as has been indicated by hatching at 28 in FIG. 8, and will increase considerably the absorption ability. As an alternative to or together with this filling of an absorbing material such material can be introduced into the double-folded layer 24 and-/or the double-folded layer 27, FIG. 8.

This can be done in the manner shown in FIG. 10. The web 13 is of a composite construction and in that case can comprise a wider web 13A of a strong material such as a non-woven material, and a narrower web 13B of a highly absorbent material such as fiber material or a polymer. The wider web is folded around the narrower web at 13'. In the finished product according to FIG. 8, the double layers 24 and 27 accordingly will contain an absorbing material enclosed by strong material and may be corrugated. Possibly, the narrower web may be limited to two strips which are covered by the folded-over marginal portions of the wider web. Such a strip is indicated by a dot-and-dash line 29 in FIG. 10 and is identified by hatching.

FIGS. 11A and 11B together show, somewhat diagrammatically, an apparatus for the manufacture of the absorbing product according to the present invention in the manner described with reference to FIGS. 1 to 7, said apparatus being constructed to operate to a great extent without attendance and to compensate for operational disturbances in one part or the other of the apparatus. Two reels of material 30A and 30B in this case are arranged to illustrate how the apparatus when one reel has been consumed, can initiate automatically the supply of material from the other reel. The material can consist of conventional gauze, but as mentioned above also other materials in the form of webs can be used. It is also conceivable to supply the material simultaneously from both reels so that the web material included in the product is a double layer material and consists of two layers of one and the same material or of two layers of different materials as according to FIG. 10. In the description to follow it is assumed, however, that the reels 30A and 30B shall alternate as to the supply of web material to the apparatus. The apparatus shown has three identical end stations 31A, 31B, and 31C, but the number of such end stations may vary from one station to a number of stations exceeding three in dependence on the desired capacity and the operating time that is possible without attendance. This is true also as far as the number of supplying reels is concerned; a single reel can be arranged and a number of reels exceeding two can be incorporated into the apparatus.

Two rollers 32A pull the web of material 33A from the reel 30A past folding plates 34A to form the folded marginal portions 13', FIGS. 1 and 10, while the web is being advanced. If the material is of the non-woven type which has no loose threads at the margins, it is not necessary to fold the web 33A and in that case the folding plates 34A can be dispensed with. The advanced web 33A passes over a guide plate 35A to the nip between the upper run of a belt conveyor 36 and the lower run of a belt conveyor 37A for advancing the web between the two belt conveyors, a support plate 38A being arranged below the web at the passage thereof between the two belt conveyors. The web continues to and through the nip between the lower run of a belt conveyor 37B and the upper run of the belt conveyor 36 over a support plate 38B, the conveyor 37B being associated with the reel 30B. From this reel a web of material 33B can be advanced by means of two rollers 32B past folding plates 34B in the same manner as described with reference to the reel 30A, but it is assumed here that this web is not used for the time being in the apparatus which could as well, however, operate with the web 33B or with both webs 33A and 33B at the same time as mentioned above.

The conveyors 36 and 37B are followed by a knife roller 39 with a counter roller 40 which are driven synchronously, but the rotational speed of which can be adjusted to the belt speed of the conveyors 36, 37A, and 37B. The rollers 39 and 40 cut the web 33A to the web pieces 13 which are to be formed to the product in the manner described with reference to FIGS. 1 to 8, and the higher the rotational speed of the rollers 39 and 40 is in relation to the belt speeds of the conveyors 36, 37A, and 37B, the shorter the web pieces 13.

The rollers 39 and 40 are followed by a belt conveyor 41 the upper run of which passes under a pressure rail 42 to advance the web pieces 13. The belt conveyor 41 is driven synchronously with the conveyors 36, 37A, and 37B and advances the web pieces to the three end stations 31A, 31B, and 31C. The transport of the web pieces to these stations is effected by means of a belt conveyor 43 the lower run of which co-operates with the upper run of three belt conveyors 44A, 44B, and 44C associated each with one of the stations 31A, 31B, and 31C, and a conveyor 44D which is in this case a discharge conveyor for web pieces which for one reason or the other have not been forwarded to one of the three stations. Since the web pieces to be carried on to the end stations should have a space between web pieces following one on the other, the conveyors 43 and 44A, 44B, 44C, and 44D have a higher speed than the conveyors 36, 37A, 37B and 41 so that the web pieces are spaced apart when they are gripped in the nip between the conveyor 43 and the conveyor 44A due to the fact that they are accelerated at the same time as they are withdrawn from the conveyor 41. This implies that the pressure rail 42 provides a reasonable pressure only to the web pieces on the upper run of the conveyor 41.

Each end station 31A, 31B, and 31C is associated with a gate 45A, 45B, and 45C which can be adjusted between operative and inoperative positions. In FIG. 11B, the gate 45A is shown in the operative position while the gates 45B and 45C are shown in the inoperative position. Preferably, the belt conveyor 43 comprises several narrow ropes arranged side by side, and the gate comprises fingers which in the operative position thereof project upwards between the ropes to catch web pieces arriving between said ropes and the conveyors 44A, 44B, and 44C, while the fingers in the inoperative position thereof are located below the ropes and do not engage with the arriving web pieces. The gate 45A when in the operative position thus will divert an arriving web piece 13 such that it will land on the belts 15 and 16 running over two conducting rollers 46 and 47 and tensioned by means of a tensioning roller 48. The belts 15 and 16 run over the mandrel 12A, 12B in the manner described above so that the web piece 13 is wound to a cartridge around the mandrel and is further treated as described with reference to FIGS. 2 to 7. The finished products according to FIG. 8, designated 49 in FIG. 11B, are supplied to a collecting container 50 located on a transverse belt conveyor 51.

When the gate 45A has transferred a web piece to the station 31A, it is immediately adjusted to the inoperative position and the plate 45B is adjusted to the operative position for the supply of a web piece to the station 31B, and when this has been done, the gate 45B returns to the inoperative position and the gate 45C is adjusted to the operative position to transfer in turn a web piece. When this has been done, the procedure is repeated by the gate 45 being again adjusted to the operative position. The treatment of the web pieces in the end station 31B and 31C is identical with that which takes place in the end station 31A.

If an end station should not receive a web piece due to some fault, an advanced web piece can pass all end stations and can be discharged into a collecting container 52 via the belt conveyor 44D. When the apparatus is started up, a first web piece which does not have the correct length, can pass directly to the container 52. The length of the web pieces can be sensed electronically in a known manner following the rollers 39 and 40, and the signals then obtained can be used together with other control signals to control all operations of the apparatus described. This can be done by means of a microprocessor and electronic sensors connected therewith which sense the supply of web pieces to the end stations, the discharge of finished round wipe-off pads therefrom, the termination of a material reel for changing to the next reel, etc. The control has not been shown or described in detail here, because such control at the present state of the art of electronics and process control technique can be arranged by the man skilled in the art by using common knowledge.

The apparatus described can be constructed with the desired capacity by a suitable choice of the number of end stations and by corresponding adjustment of the speeds of the belt conveyors to the number of end stations. The period during which the apparatus can operate without attendance will be dependent on the number of end stations and the number of web reels arranged in the apparatus. Preferably, the microprocessor is arranged to reduce the advancing speed of the web pieces if an end station fails due to some fault therein such that the web pieces are supplied as rapidly as they are treated in the remaining end stations instead of being partly discharged into the container 52 without having been treated. In the embodiment described having three end stations, the microprocessor thus should reduce the capacity to ⅔ if one end station fails, and to ⅓ if two end stations fail and should stop the machine completely if all three end stations fail.

Referring to FIG. 10, a so-called X-ray contrast wire 53 can be located in any of the folds formed when the wider material web 13A is being folded. It has been indicated also in FIG. 8 and will lay either in the double fold 24 or in the double fold 27 depending on the edge of the web at which it is located. The wire serves the purpose to indicate, when a patient is being X-rayed, a round wipe-off pad, if any, which has been forgotten at a surgical operation. As a supplementary safety measure the absorbing product according to the invention when it comprises a round wipe-off pad, can be provided with a string 54 according to FIG. 12. How this string is attached to the product will be described with reference to FIGS. 13 to 15.

According to FIGS. 13 to 15, an axial passage 55 is arranged through the ejector piston 22 for the passage of the string 54 which passes through the mandrel element 12A to a string guide 56 which holds the string but allows withdrawal of the string from the string guide against a controlled resistance. When the material piece 13 is engaged with the two mandrel elements 12A and 12B to be wound to a cartridge 17 around the combined mandrel as described with reference to FIG. 2, the leading edge of the material piece will catch the string 54 so that the string will be wound together with and around the material piece in the gap between the two mandrel elements, the string being withdrawn from the string guide 56 against a resistance determined by the string guide. Due to the resistance in the string guide 56 the string will purse up the material piece in the gap between the mandrel elements as shown in FIG. 14. When the product has been finished in the manner described with reference to FIGS. 2 to 7 and is ejected from the cavity 31 by axial displacement of the ejecton piston 22, the string 54 attached to the finished product, will be advanced through the passage 55 in the piston 22, a carrier 57 then engaging the string 54 and pulling out the string through the string guide 56 so as to form a loop thereof. The carrier is provided with a cutter 58 co-operating with a stationary cutter 59 for cutting off the string.

If the string 54, when a product has been manufactured in the manner described with reference to FIGS. 13 to 15, is not pulled out to form a loop by means of the carrier 57 in the manner shown in FIG. 15, but a further product is manufactured with the string extending axially through the mandrel, this latter product will be displaceably arranged on the string. An arbitrary number of absorbing products thus can be arranged on a single string as is shown in FIG. 16. Such a "chain product" can be used as a substitute for a so-called abdominal cloth at surgical operations, but it can also be used in order to limit liquid spillage on the floor or the ground or oil spillage on the water depending on the size of the product and the material from which it is made.

FIG. 17 discloses a tampon which is made in a manner which principally is a modification based on the embodiments according to FIGS. 8 and 9. In this case a double layer has been provided by advancing the layer 24', FIG. 9, so far that it has been twisted into the twisted portion 26. Between the layers 24' and 25, FIG. 9, an absorbing material 59 has been included which is completely enclosed between the layers 24' and 25. The absorbing material 59 can be supplied to the mandrel together with the material piece 13.

Also the embodiment of the tampon in FIGS. 18 and 19 is a modification of the absorbing product according to the invention, which is based on the embodiments according to FIGS. 8 and 9. In this case absorbing material 28 is included in the same manner as in FIG. 8 and absorbing material 60 is introduced into the double layer 24, the folding of this layer being extended to the twisted portion 19 and being twisted into said portion. The outermost layer in FIG. 18 comprises a single layer 27', but also a double layer 27 can be arranged in this case with an absorbing material included therein. In that case the folding of the layer 27 can be extended to the twisted portion 26 and can be twisted into said portion.

In FIG. 18, the string 54 forms a loop and FIGS. 20 and 21 disclose how this loop is obtained.

In this case a double string 54 is drawn into the combined mandrel by means of a carrier 61 operating in the transverse direction of the mandrel in the gap between the mandrel elements, the string passing through the string guide 56. Inside the mandrel the string is caught by the rod 23 arranged as a string carrier, which introduces the string loop into the cavity 21 in the mandrel element 12A, FIG. 21. Then, the string is caught and is attached by twisting in the same manner as described with reference to FIGS. 13 and 14.

In FIGS. 22 and 23, the use of the tampon in FIG. 18 as a menstrual tampon is illustrated, said tampon being in the operative position in the vagina in FIG. 22, which is indicated at 62. At the end of a menstrual period when the fluid flow is decreasing, it may happen when conventional menstrual tampons are being used that the tampon adheres to the mucous membrane of the vagina wall due to the fact that the highly absorbing material of conventional tampons is located also in the surface layer of the tampon. When the tampon is withdrawn there is the risk of damage to the mucous membrane and of fibers being retained on said membrane. This is avoided by the tampon of the invention, because the outer layer 27' will be rolled off the mucous membrane when the tampon is withdrawn, said layer at the same time being turned inside out in the manner shown in FIG. 23. Notwithstanding the fact that the outer layer 27' in this manner leaves the enclosing position, the absorbing portions of the tampon are still enclosed in intact casings. It should be particularly noted that the material of the piece 13 which forms inter alia the layer 27' of the tampon of the invention, should be a material which does not or substantially not absorb fluid per se but on the contrary is extensively permeable to fluid such that the fluid can be sucked up by the the absorbing material 28, 60.

In order to stiffen the absorbing product according to the invention and to reduce the diameter thereof while the size of the outside surface area is being maintained the product can be formed as shown in FIG. 25. This can be attained by the product initially being formed according to FIG. 24 by a proper profile of the cavity 21 and the rod 23 so as to be pressed later at the ejection according to FIG. 7 through a passage which further compresses the product to the shape according to FIG. 25.

I claim:

1. An absorbing product comprising: a substantially cylindrical cartridge of a web material having two ends and including a first covering layer of said web material, a second covering layer of said web material, a first twisted portion joining the first and second covering layers at one end of the cartridge, said second layer being folded back from said first twisted portion to be located at one side of said first layer, a second twisted portion at the other end of the cartridge, and a third layer of said web material joining said first layer at the second twisted portion and folded back therefrom in a direction opposite to said second layer to form the outside surface of the cartridge, said first layer defining a closed cavity between said first and second twisted portions.

2. Product as claimed in claim 1 wherein said second and third layers have folded marginal protions.

3. Product as claimed in claim 2 wherein a string is attached between the layers in one of the twisted portions.

4. Product as claimed in claim 1 wherein at least one of the second and third layers is fixed in the twisted portions at the two ends of the product.

5. Product as claimed in claim 1 wherein the web material comprises a plurality of layers having different properties.

6. Product as claimed in claim 1 wherein the cavity contains an absorbing particulate or fibrous material.

7. Product as claimed in claim 2 wherein the folded marginal portions enclose an absorbing particulate or fibrous material.

8. Product as claimed in claim 1 wherein at least the second and third layers are corrugated.

* * * * *